United States Patent [19]

Tieckelmann et al.

[11] Patent Number: 5,061,483

[45] Date of Patent: Oct. 29, 1991

[54] PERMANENT WAVE HAIR COMPOSITIONS CONTAINING TRANSITION METAL OXIDE COMPOUNDS

[75] Inventors: Robert H. Tieckelmann, Trenton, N.J.; Mary Ann Perini, West Haverstraw, N.Y.

[73] Assignee: Chesebrough-Pond's USA Co., Greenwich, Conn.

[21] Appl. No.: 517,097

[22] Filed: May 1, 1990

[51] Int. Cl.$^5$ .................... A61K 7/09; A45D 7/04
[52] U.S. Cl. ................................ 424/72; 132/204; 132/209; 8/127.51
[58] Field of Search .............. 424/71, 72; 132/203, 132/204, 209; 8/127.51

[56] References Cited

U.S. PATENT DOCUMENTS

| | | | |
|---|---|---|---|
| 2,087,953 | 7/1937 | Malone et al. | 132/202 |
| 2,183,894 | 12/1939 | Pye | 132/203 |
| 2,261,094 | 10/1941 | Speakman | 132/204 |
| 2,540,980 | 2/1951 | Den Beste et al. | 132/203 |
| 2,707,697 | 5/1955 | Wainer | 424/71 |
| 2,739,033 | 3/1956 | Lubs | 424/71 |
| 2,850,351 | 9/1958 | Moore et al. | 8/127.6 X |
| 4,532,950 | 8/1985 | Lang et al. | 132/204 |
| 4,770,872 | 9/1988 | Hsiung et al. | 424/72 |

FOREIGN PATENT DOCUMENTS 0113992 7/1984 European Pat. Off. .
1198012 8/1965 Fed. Rep. of Germany .

OTHER PUBLICATIONS

Patterson et al., J. Res. Nat. Bur. Stand., 27:89.
Spence et al., Inorg. Chem., 2 (1963).

*Primary Examiner*—Thurman K. Page
*Assistant Examiner*—Susan S. Rucker
*Attorney, Agent, or Firm*—Rimma Mitelman

[57] ABSTRACT

Keratinous material, such as human hair, in which disulfide linkages have been ruptured to form sulfhydryl groups can be permanently set using transition metal oxide compounds.

20 Claims, No Drawings

PERMANENT WAVE HAIR COMPOSITIONS CONTAINING TRANSITION METAL OXIDE COMPOUNDS

BACKGROUND OF THE INVENTION

1. Field of the Invention

The present invention relates to the treatment of keratinous material, such as attaining permanently waved or straightened hair.

2. The Related Art

Keratin is a major constituent of horns, hoofs, nails and feathers and mammalian hair, such as wool or human hair. Keratin consists of long polypeptide chains crosslinked to one another by cystine disulfide linkages, the crosslinkages conferring structural rigidity on a keratin-containing material.

Permanent hair deformation, i.e. permanent waving and permanent straightening, involves rearrangement of the keratin polypeptide chains.

Hot waving methods employ heat above 140° F., frequently as high as 300° F., and the action of steam and alkali. Hot waving methods have virtually disappeared because they are too complicated and are excessively damaging to the hair. Moreover, hairdressers can not be certain with such methods that the desired results would consistently be obtained. Hot waving, therefore, has gradually been replaced by cold waving.

Permanent hair straightening is sometimes done using a hot metal comb and covering the hair with lipid compounds or an emulsion. More frequently, straightening gels or emulsions containing various proportions of strong bases are used. These permanent hair straightening methods are irritant to the scalp, and careless handling may cause hair damage. Straighteners are sometimes formulated like cold wave products.

In cold permanent waving or straightening, disulfide crosslinkages in hair keratin are ruptured by using various reducing agents. Common reducing agents include inorganic sulfides, sulfites, hydrosulfites, cyanides, mercaptans, thioglycolic acid and various other compounds. Sulfhydryl groups are formed in place of the disulfide linkages. The shaping of the hair into a desired conformation has conventionally been carried out by contacting the hair with a reducing agent in the form of liquids, creams or gels while the hair has been mechanically formed into the desired new shape. The reducing composition is applied to the hair for a sufficient time to allow shaping to occur by the reductive disruption of the disulfide linkages. Finally, disulfide crosslinkages are reformed or novel disulfide linkages are created by applying to the hair oxidizing or crosslinking agents, while maintaining hair in a form which it is desired to render permanent. The final step of establishing disulfide crosslinkages, which may be referred to as the neutralizing or fixing step, is important in order to make the new conformation permanent, to increase tensile strength, to avoid damage to the hair and to remove the sulfhydryl groups as reactive sites.

Oxidative crosslinking employs a number of the usual chemical oxidizing agents or atmospheric oxygen to convert sulfhydryl groups to the corresponding disulfide. Hydrogen peroxide, perborate and bromates have been widely used in permanent hair deformation. Oxidation of sulfhydryl groups with chemical oxidizing agents may be catalyzed by metals. German Patent 1,198,012 discloses the use of small amounts of alkali metal metavanadates, i.e. 0.00025% by weight, to catalyze the bromate-based oxidation of hair.

The oxidative method employing atmospheric oxygen, termed "self-neutralizing", depends on air oxidation to destroy any reducing agent on the hair and to reform disulfide linkages. This method does not necessitate subsequent application of a separate neutralizing solution to the hair; self-neutralizing waving lotions sometimes include metal catalysts in addition to a reducing agent. Den Beste et al., U.S. Pat. No. 2,540,980 and Lang et al., U.S. Pat. No. 4,532,950 disclose addition of manganese chloride or sulfates of cobalt, copper or iron as oxidation catalysts to a waving lotion containing a reducing agent. Wainer, U.S. Pat. No. 2,707,697 discloses incorporation of iron sulfate in a waving lotion containing citric acid. Self-neutralizing waving lotions are poorly suited for professional use or for hair straightening applications and have not gained consumer acceptance.

It is also possible to convert sulfhydryl linkages to disulfide crosslinkages in a non-oxidative manner by using crosslinking agents such as alkylene dihalides or dihalocarboxylic acids as in U.S. Pat. No. 2,739,033 or dimaleimides as in U.S. Pat. No. 2,850,351. Speakman, U.S. Pat. No. 2,261,094 discloses the use in permanent hair waving of polyvalent metals, namely, sulfates of bivalent metals, such as calcium, barium, zinc, copper and nickel. In practice, when bivalent metal sulfates disclosed by the Speakman patent are employed, it has been found desirable to mix such crosslinking reagents with traditional oxidizing agents, such as hydrogen peroxide. The Speakman patent teaches desirability of such mixtures to reduce the time of treatment at col. 4, lines 10-17. Moreover, crosslinkages of bivalent metals with sulfur atoms have been considered ionic and unstable by Patterson et al., J. Res. Nat. Bur. Stand., 27:89. Complexes of dissolved cysteine (reduced cystine) with molybdenum in aqueous solution in the pH range of 4 to 6 have been described by Spence et al., Inorg. Chem., 2 (1963) 319. Spence et al. observed little complex formation above pH 6.5.

Many neutralizing agents which have been proposed heretofore are toxic and thus are difficult to employ. Others are volatile and may be hazardous to use. A crosslinking reagent is desirable that is not encumbered by the difficulties of the past but is as effective as traditional oxidizing treatments.

Therefore, it is an object of the present invention to provide a crosslinking composition for forming disulfide linkages in a keratinous material in which disulfide linkages have been disrupted and replaced by sulfhydryl groups.

It is a further object of the present invention to provide a product for permanent hair waving or straightening comprising a composition for reducing disulfide bonds to form sulfhydryl groups and the aforementioned crosslinking composition.

A still further object of this invention is to provide a method for treating a keratinous material in which disulfide linkages have been ruptured, which method includes contacting the keratinous material with the aforementioned crosslinking composition.

These and other objects will become more apparent by consideration of the detailed description and examples that follow.

SUMMARY OF THE INVENTION

The attainment of the above objects is made possible by this invention which includes a crosslinking composition containing a transition metal oxide compound. The crosslinking composition of the invention converts sulfhydryl groups to disulfide crosslinkages in the keratinous material in which sulfhydryl groups have been previously formed by rupturing disulfide linkages.

The inventive method for treating a keratinous material includes a step of contacting the crosslinking composition containing an effective amount of a transition metal oxide compound with the keratinous material in which disulfide linkage have been previously disrupted.

According to this invention, the crosslinking composition may be included in a product for permanent hair deforming such as permanent hair waving or permanent hair straightening, the product also containing a reducing composition to effect disruption of disulfide crosslinkages and formation of sulfhydryl groups.

While a wide group of keratin-containing materials and articles made therefrom can be treated in accordance with the present invention, including animal hair such as camel hair, mohair, wool, horsehair, cattle hair, hog bristles and the like; and feathers such as from chicken, duck, turkey and the like, the invention is particularly directed to waving or straightening human hair whether in vivo or in vitro, i.e. in the form of wigs. The invention is particularly directed to cold waving and hair straightening systems and will be discussed in connection therewith. The inventive composition, product and method can be used professionally in beauty salons or by unskilled consumers in their own homes.

DESCRIPTION OF THE INVENTION

Herein is disclosed a crosslinking composition containing a transition metal oxide compound, useful for forming disulfide crosslinkages in keratinous material in which disulfide linkages have been previously ruptured.

The essential component of the inventive composition is a transition metal oxide compound.

Although the exact nature of the species formed when reduced hair is contacted with a solution of transition metal oxide compound is not known, it is proposed that a transition metal ion, oxygen and sulfur form a mixed complex. Such complexes are stable, unlike ionic bonds of bivalent metal cations with sulfur described in U.S. Pat. No. 2,261,094, i.e. hair deformation is rendered permanent and resistant to moisture and alkali.

Transition metal oxide compounds wherein a transition metal ion is chosen from groups 4b–6b of the Periodic Table, such as molybdenum, vanadium and tungsten are particularly suitable for use in this invention, molybdenum being most preferred.

The following list is illustrative of the transition metal oxide compounds employed in this invention, suppliers indicated in parenthesis:

Ammonium Molybdate, $(NH_4)_6 Mo_7O_{24} \times 4H_2O$, (Aldrich Chemical Co., Alfa Products, Fisher Scientific)
Ammonium Molybdate VI, $(NH_4)_2MoO_4$, (Aldrich Chemical Co., Alfa Products, Fisher Scientific)
Ammonium Tungstate, $(NH_4)_2WO_4$, (Aldrich Chemical Co.)
Ammonium Vanadate, $NH_4VO_3$, (Fisher Scientific)
Potassium Tungstate, $K_2WO_4$, (Alfa Products)
Sodium Orthovanadate, $Na_3VO_4$, (Aldrich Chemical Co.)
Sodium Metavanadate, $NaVO_3 \times nH_2O$, (Aldrich Chemical Co.)
Sodium Tungstate, $Na_2WO_4$, (Aldrich Chemical Co.)
Sodium Molybdate, $Na_2MoO_4$, (Aldrich Chemical Co.)
Vanadyl Sulfate, $VOSO_4 \times nH_2O$ (Fisher Scientific)
Potassium Molybdate, $K_2MoO_4$, (Alfa Products)

Of course, other transition metal oxides may be employed. Ammonium molybdate is most preferred due to its availability and performance.

The transition metal oxide compound is incorporated in the crosslinking composition of the invention in an effective amount to crosslink a sufficient amount of sulfhydryl groups to permanently set the keratinous material. Preferably, the amount of transition metal oxide compound in the crosslinking composition is about 0.01% to about 10% weight per volume, most preferably about 0.5% to about 5%. As used herein the term "% weight per volume" is intended to mean "grams per 100 milliliters".

The crosslinking composition of the invention is useful whenever it is desirable to render permanent a particular rearrangement of keratin polypeptide chains and is particularly useful in products or processes for cold permanent hair waving or straightening. Advantageously, the crosslinking composition of the invention is as effective in forming stable disulfide linkages as traditional oxidizing agents such as hydrogen peroxide or bromates. Thus, the crosslinking composition of the invention is effective even in the absence of traditional oxidizing agents.

The crosslinking composition can also contain a wetting agent or surfactant which is non-reactive with the crosslinking reagent or the hair to destroy crosslinking sites. The surfactant can be anionic, such as soaps, and alkyl sulfates, such as sodium dodecyl sulfate; cationic such as quaternary ammonium compounds; nonionic, such as glycol esters, glycerol esters, sorbitan esters, polyoxyalkylene esters, polyoxyalkylene ethers, and modified lanolin, as well as amphoteric surfactants. The surfactant is used in an amount of about 0.1% to about 60%, the amount being sufficient to assist in wetting the hair with the crosslinking reagent, depending on the efficiency of the surfactant.

According to this invention, the crosslinking composition may be a part of the product for permanent hair deforming and the product may be conveniently formulated and packaged to provide a complete treatment of hair resulting in permanently waved or straightened hair.

The product of the invention necessarily contains the inventive crosslinking composition and a separate reducing composition for forming sulfhydryl groups in place of disulfide crosslinkages.

The reducing agents most commonly used in cold waving hair lotions for rupturing cystine linkages are thiols or mercaptans as well as sulfites and/or bisulfites. A number of mercaptans can only provide acceptable efficiency at high pH levels whereas others with a lower pK and a high ionization constant can be effective at lower pH levels. For example, the ammonium salt of thioglycolic acid can provide acceptable waving efficiency (reduction) if the pH of the solution exceeds 9. Other compounds such as thioglycolamides or glycol thioglycolates, sulfites and/or bisulfites can be used at neutral or slightly acidic pH. The following are mercaptans and thiols which have commonly been used in cold waving lotions: thioglycolic acid or salts thereof, thiolactic acid, cysteine, thioglycerol, thioglycolic hydrazide, thioglycolamide, glycerol monothioglycolate, beta-mercapto-propionic acid, N-hydroxyethyl mercapto-acetamide, N-methyl mercapto-acetamide, beta-mercapto-propionamide, 2-mercapto-ethanesulfonic acid, dimercapto-adipic acid, dithiothreitol, homocysteinethiolactone, cysteine derivatives, and polythiol derivatives formed by the addition of cysteamine onto a maleic anhydride-alkylvinylether copolymer. The sulfites and/or bisulfites which can be used are those normally used in hair waving such as sodium and ammonium salts. The amount of the reducing agent used is that sufficient to rupture a sufficient number of disulfide bonds for effective hair waving or hair straightening as would be appreciated by one of ordinary skill in the art. Preferably, the amount of reducing agent employed is between about 1% and about 20%, most preferably between about 7.5% and 11% at a pH between about 9.3 and about 9.5, the concentration being adjusted to the quality of the hair to be deformed. For example, bleached hair, which is very porous, brittle, and lacking in disulfide linkages, must be treated with low concentration of a reducing agent.

Reducing and crosslinking compositions based on the actives described above can be prepared in various physical forms including lotions, solutions, creams, gels, aerosols and dry forms.

By the breaking of the disulfide bonds to form free sulfhydryl groups pendant on the hair, the hair can be formed or shaped as desired such as by winding on rollers or pins, or combed out as in the case of hair straightening. The breaking of the disulfide bonds is generally accomplished in accordance with the usual practice, which involves applying the reducing agent to the hair wound on curlers. Heat can be provided at this point.

The deformed hair, while curled or straightened, is then wetted with the crosslinking composition of the invention in water or a pharmaceutically acceptable carrier or base such as lotion or cream, preferably buffered. The crosslinking composition is preferably water-soluble or made water soluble by known techniques. The carriers are of known types and are similar to those presently in use in waving and neutralizing compositions. The water or carrier desirably holds the crosslinking reagent in contact with the hair for a period of time sufficient to effect permanent setting of the hair. The crosslinking composition is applied under conditions conducive to effective crosslinking. A pH of between about 6 and about 9 (less than that which would cause permanent breakdown of the hair protein) has been found effective for that purpose using the composition of the invention.

Reducing compositions based on the actives described above can be prepared in various physical forms including lotions, solutions, creams, gels, aerosols and dry forms.

Any or a combination of alkali metal phosphates, acetates, borates and the like which are non-reactive with the crosslinking reagent and cannot destroy crosslinking sites, can be used to maintain the pH of the hair treated with the crosslinking composition within the range specified. Any pH effects caused by the reducing agent can be offset by thorough washing of the hair with water prior to the application of the crosslinking composition.

The hair is treated for a period of time sufficient to effect the crosslinking to provide the desired permanent shape desired and, in some instances, the desired tensile strength increase. Illustrative times include from about 3 minutes to any time practical that avoids deterioration of the hair, though lesser times can be used if lesser effect on the hair is desired.

The crosslinking reagent is preferably applied in aqueous solution at a temperature between the ranges of about 10° C. and 93° C. Time of treatment may vary within wide limits depending on the temperature of the solution, the particular reducing and crosslinking agents used, and the nature of the keratinous material being treated.

The hair may be further treated with additional neutralizing agents and crosslinking reagents in order to oxidize any free sulfhydryl groups to disulfide linkages as would be appreciated by one of ordinary skill in the art. The oxidizing or neutralizing chemicals used can be any of the oxidizing agents capable of restoring the disulfide linkages in the hair keratin during the resetting state, such as aqueous solution of hydrogen peroxide, alkali metal bromates, alkali metal perborates, urea hydrogen peroxide, sodium sesquicarbonate, etc. Rinsing alone with water may restore the broken linkages as well, but it will be much slower. However, as pointed out above the crosslinking compositions of the invention are effective in the absence of peroxygen or bromate oxidizing agents.

The permanent hair deforming product of the invention can be designed for professional as well as home application. The product and its compositions can contain ingredients normal to such compositions. Fragrance compounds, coloring agents, thickening agents, opacifying agents, sequestering agents, solubilizing agents, gelling agents, surfactants, conditioning agents, such as amino acids, proteins, and silicones, mineral oils and the like may be added to compositions of this invention in amounts conventionally used in hair waving and straightening compositions. Any compound which will react with the crosslinking reagent to remove or neutralize reactive sites thereon is preferably avoided. These ingredients are fully outlined in The Science of Hair Care, edited by Charles Zviak, Vol. 7 of a series entitled Dermatology, Marcel Dekker, Inc., 1986, which is incorporated herein by reference.

The Examples which follow illustrate the present invention in greater detail. However, it should be understood that the present invention in its broadest aspect is not necessarily limited to these Examples.

EXAMPLE I

Swatches (40 milligrams; 8.1 inches in length) of European brown Caucasian hair were wrapped around curling rods and treated with various commercially available permanent wave products according to manufacturers' instructions. All products tested utilize thioglycolate in a reducing composition and hydrogen peroxide in a neutralizing composition of the hair. Typical treatment time for a neutralization step is 5 to 10 minutes.

Following the treatment, the standard evaluation procedure was employed as follows:

The swatches were unrolled from curlers, straightened by hand, trimmed to length of 7 inches and hung to dry for 24 hours. The swatches were then suspended for 2 hours in a 4-liter beaker containing 2 drops of 29% sodium lauryl sulfate in 4 l of cold tap water. The swatches were hung to dry for 24 hours and the final dry curl length was measured. All measurements were done from the edge of the tape.

Data that was generated is summarized in Table I. Products tested were ranked per final dry curl length.

TABLE I

| Product | Final Dry Curl Length (inches) |
| --- | --- |
| LOREAL ® | 5.8–6.0 |
| LILT ® | |
| CLAIROL PROFESSIONAL ® | |
| REVLON ® | 6.1–6.5 |
| TONI ® | |

Commercial formulations employing hydrogen peroxide resulted in final dry curl length of about 5.8 inches to about 6.5 inches.

EXAMPLE II

Swatches (40 milligrams; 8.1 inches in length) of European brown Caucasian hair were wrapped around curling rods and treated with commercially available thioglycolate waving lotion LOREAL ® (normal hair) for 20 minutes to rupture the disulfide crosslinkages. The swatches were then rinsed for 2 minutes with running tap water and immersed in aqueous solutions of various neutralizing agents at room temperature.

Final dry curl length of the swatches was evaluated according to the standard procedure described in Example I. Data that was generated is summarized in Table II.

TABLE II

| Sample # | Neutralization Agent | Neutralization Time (minutes) | Final Dry Curl Length (inches) |
| --- | --- | --- | --- |
| 1 | Water | 2 | 6.4 |
| 2 | 2% Hydrogen Peroxide | 5 | 5.7 |
| 3 | 5% Ammonium Molybdate | 5 | 5.9 |

At room temperature, final dry curl length obtained with ammonium molybdate was equal, within the experimental error, to final dry curl length obtained with hydrogen peroxide and significantly better than the final dry curl length obtained if a neutralizing agent is omitted (sample 1). The final dry curl length (5.9 inches) in 5 minutes with ammonium molybdate solution was within the range of 5.8 to 6.5 inches obtained in Example I with commercial products.

EXAMPLE III

Swatches (40 milligrams; 8.1 inches in length) of European brown Caucasian hair were wrapped around curling rods and treated with commercially available thioglycolate waving lotion LOREAL ® (normal hair) for 20 minutes to rupture the disulfide crosslinkages. The swatches were then rinsed for 2 minutes with running tap water and immersed at room temperature in aqueous solutions of ammonium molybdate at various concentrations and for various lengths of time as indicated in Table III.

Hair swatches were evaluated for final dry curl length according to the standard procedure described in Example I. Data that was generated is summarized in Table III.

TABLE III

| Ammonium Molybdate Concentration | Neutralization Time | Final Dry Curl Length (inches) |
| --- | --- | --- |
| 0.05% | 20 minutes | 5.9 |
| 0.5% | 20 minutes | 6.1 |
| 5.0% | 20 minutes | 5.9 |
| 0.05% | 20 hours | 4.1 |
| 0.5% | 20 hours | 4.0 |
| 5.0% | 20 hours | 4.0 |

Final dry curl length was independent of concentration of ammonium molybdate. A longer neutralization period improved final dry curl length, perhaps representing effect of prolonged diffusion of ammonium molybdate into the hair fiber.

EXAMPLE IV

Swatches (40 milligrams; 8.1 inches in length) of European brown Caucasian hair were wrapped around curling rods and reduced with commercially available thioglycolate waving lotion LOREAL ® (normal hair) for 20 minutes to rupture the disulfide crosslinkages. The swatches were then rinsed for 2 minutes with running tap water, followed by a rinse with aqueous solutions of ammonium molybdate at various concentrations as indicated in Table IV. The swatches were then placed in a bag and heated in a water bath at about 50° C. for 20 minutes.

Hair swatches were evaluated for final dry curl length according to the standard procedure described in Example I. Data that was generated is summarized in Table IV.

TABLE IV

| Sample # | Ammonium Molybdate (% Concentration) | Final Dry Curl Length (inches) |
| --- | --- | --- |
| 1 | 0.05 | 5.1 |
| 2 | 0.5 | 5.0 |
| 3 | 5.0 | 4.8 |

Application of heat in neutralization step improved performance of ammonium molybdate when compared to samples 1, 2 and 3 of Example III.

EXAMPLE V

Reduced hair treated with ammonium molybdate was studied using atomic absorption spectroscopy (AAS) and photoelectron spectroscopy (PES).

Hair swatches (0.5 g) were reduced with LOREAL ®, rinsed with tap water and immersed in ammonium molybdate for 72 hours. Other hair swatches, used as control, were reduced with LOREAL ®, rinsed with tap water, neutralized according to LOREAL ® instructions with hydrogen peroxide for 10 minutes and thereafter aged with ammonium molybdate treated samples. After 72 hours all swatches were rinsed with tap water and allowed to air-dry. The swatches were analyzed using AAS and PES.

AAS analysis detected no molybdenum in the control sample. 0.4% (3600 ppm) of molybdenum was absorbed in molybdenum treated samples.

PES confirmed that molybdenum was present in the molybdenum-treated sample and evenly dispersed throughout the hair sample.

EXAMPLE VI

Swatches (40 mg, 8.1 inches in length) of European brown Caucasian hair were wrapped around curlers and reduced with 0.6 N thioglycolic acid solution, adjusted to pH 9.4 with concentrated ammonium hydroxide. The reduction was performed at room temperature for 20 minutes. After a rinse with warm tap water (37° C.), the hair swatches were rinsed with a neutralizing candidate and allowed to react for 20 minutes at either room temperature or 50° C. A warm rinse followed the neutralization step. Final dry curl length of the hair swatches was evaluated using the standard procedure described in Example I.

Data that was generated is summarized in Table VI.

TABLE VI

| Neutralization Agent | Final Dry Curl Length (Inches) |
|---|---|
| Control[1] | 5.5 + 0.1 |
| Ammonium molybdate | 5.2 |
| Sodium molybdate | 5.3 |
| Potassium molybdate | 5.4 |
| Vanadyl sulfate | 5.3 + 0.3 |
| Ammonium vanadate | 4.8 + 0.4 |
| Sodium metavanadate | 5.1 + 0.1 |
| Sodium orthovanadate | 4.5 + 0.6 |
| Potassium tungstate | 4.6 |

[1]Combination of $H_2O$ and $H_2O_2$ treatments at 50° C. and at room temperature.

Transition metal oxide compounds are equal to or better than water and/or hydrogen peroxide when used as neutralizing agents for reduced hair keratin.

The foregoing description and Examples illustrate selected embodiments of the present invention and in light thereof variations and modifications will be suggested to one skilled in the art, all which are in the spirit and purview of this invention.

What is claimed is:

1. A crosslinking composition for forming disulfide linkages in a keratinous material in which disulfide linkages have been disrupted to form sulfhydryl groups, said composition comprising a transition metal oxide compound in an amount of about 0.01% to about 10% weight per volume.

2. A composition of claim 1 wherein said keratinous material is human hair.

3. A composition of claim 1 further comprising a pharmaceutically acceptable carrier for said transition metal oxide compound.

4. A composition of claim 1 wherein said transition metal oxide compound contains a transition metal ion chosen from groups 4b-6b of the Periodic Table.

5. A composition of claim 4 wherein said transition metal ion is molybdenum.

6. A composition of claim 1 wherein said transition metal ion is vanadium.

7. A composition of claim 1 wherein said transition metal ion is tungsten.

8. A hair deforming product comprising:
    (a) about 1% to about 20% of a reducing agent for reducing disulfide bonds to form sulfhydryl groups in the hair; and
    (b) a transition metal oxide compound in an effective amount sufficient to set the hair permanently,
    wherein components (a) and (b) are contained in separate compositions.

9. A product of claim 8 wherein the amount of said transition metal oxide compound is about 0.01% to about 10% weight per volume.

10. A product of claim 8 wherein said transition metal oxide compound contains a transition metal ion selected from groups 4b-6b of the Periodic Table.

11. A product of claim 8 wherein said transition metal ion is vanadium.

12. A product of claim 8 wherein said transition metal ion is tungsten.

13. A product of claim 8 wherein said transition metal ion is molybdenum.

14. A method for treating keratinous material in which disulfide linkages have been disrupted, said method comprising contacting said keratinous material with a composition comprising a transition metal oxide compound in an amount of about 0.01% to about 10% weight per volume.

15. A method of claim 14 wherein said transition metal oxide compound contains a transition metal ion selected from groups 4b-6b of the Periodic Table.

16. A method of claim 15 wherein said transition metal ion is molybdenum.

17. A method of claim 15 wherein said transition metal ion is vanadium.

18. A method of claim 15 wherein said transition metal ion is tungsten.

19. A method of claim 15 wherein said disulfide linkages have been disrupted by treating said material with an effective amount of a reducing agent.

20. A method of claim 19 wherein said reducing agent is selected from the group consisting of thioglycolic acid or salts thereof, thilactic acid, cysteine, thioglycerol, thioglycolic hydrazide, beta-mercapto-propionic acid, N- hydroxyethyl mercapto-acetamide, N-methyl mercapto- acetamide, beta-mercapto-propionamide, mercapto- ethanesulfonic acid, dimercapto-adipic acid, dithiothreitol, homocysteinethionlactone, cysteine derivatives and polythiol derivatives formed by the addition of cysteamine onto a maleic anhydride-alkyl-vinylether copolymer, sulfites, sulfites and mixtures thereof.

* * * * *